(12) United States Patent
Toivonen et al.

(10) Patent No.: US 12,286,522 B2
(45) Date of Patent: Apr. 29, 2025

(54) HIGHLY SCATTERING POROUS MATERIAL BASED ON FIBRILLAR, ELONGATED, OR DISK-LIKE PARTICLES

(71) Applicants: Aalto University Foundation SR, Aalto (FI); Cambridge Enterprise Limited, Cambridge (GB)

(72) Inventors: Matti Toivonen, Aalto (FI); Olli Ikkala, Aalto (FI); Silvia Vignolini, Cambridge (GB); Olimpia Domitilla Onelli, Cambridge (GB)

(73) Assignees: Aalto University Foundation SR, Aalto (FI); Cambridge Enterprise Limited, Cambridge (GB)

( * ) Notice: Subject to any disclaimer, the term of this patent is extended or adjusted under 35 U.S.C. 154(b) by 124 days.

(21) Appl. No.: 16/647,744

(22) PCT Filed: Sep. 26, 2018

(86) PCT No.: PCT/EP2018/076186
§ 371 (c)(1),
(2) Date: Mar. 16, 2020

(87) PCT Pub. No.: WO2019/063647
PCT Pub. Date: Apr. 4, 2019

(65) Prior Publication Data
US 2020/0224001 A1    Jul. 16, 2020

(30) Foreign Application Priority Data
Sep. 26, 2017   (FI) .................................... 20175855

(51) Int. Cl.
*C08J 9/28*     (2006.01)
*C08J 9/00*     (2006.01)

(52) U.S. Cl.
CPC ............. *C08J 9/286* (2013.01); *C08J 9/0085* (2013.01); *C08J 2201/04* (2013.01); *C08J 2301/02* (2013.01)

(58) Field of Classification Search
CPC .... A61K 8/0216; A61K 8/0254; A61K 8/027; A61K 8/0275; A61K 8/0279; A61K 8/25;
(Continued)

(56) References Cited

U.S. PATENT DOCUMENTS

| 5,629,055 A | 5/1997 | Revol et al. |
| 5,858,078 A | 1/1999 | Andes et al. |

(Continued)

FOREIGN PATENT DOCUMENTS

| CN | 1696398 A | 11/2005 |
| CN | 101851801 A | * 10/2010 |

(Continued)

OTHER PUBLICATIONS

Translation of JP 2014163028 A, Mikami et al., Sep. 8, 2014. (Year: 2014).*
Translation of CN 101851801 A, Chen et al., Oct. 6, 2010. (Year: 2010).*
FI 20175855, Mar. 14, 2018, Search Report.
PCT/EP2018/076186, Mar. 31, 2020, International Preliminary Report on Patentability.

(Continued)

*Primary Examiner* — Hai Vo
(74) *Attorney, Agent, or Firm* — Wolf, Greenfield & Sacks, P.C.

(57) ABSTRACT

The present invention concerns a material, based on fibrillar, elongated, or disk-like colloidal particles, that has a high scattering efficiency, a method that is suitable for preparing such a material, and the use of such a material. The material can be used as, or as a part of, a pigment, paint or protective coating in various industries, but due to its high scattering, and due to the fact that the material appears white even as a thin membrane, it is an interesting option also in the paper and pulp, cosmetic and medical industries.

17 Claims, 10 Drawing Sheets

(58) Field of Classification Search
CPC . A61K 8/29; A61K 8/60; A61K 8/731; A61K 8/736; A61K 8/9706; A61K 8/9789; D21H 11/18; C09D 5/00; C09D 5/03; C09D 5/031; C09D 5/032; C09D 7/65; C09D 7/68; C08J 2201/04; C08J 2301/02; C08J 9/0085; C08J 9/286; C08L 1/02; C08F 6/008; C08H 8/00
See application file for complete search history.

(56) References Cited

U.S. PATENT DOCUMENTS

| | | |
|---|---|---|
| 2009/0305033 A1 | 12/2009 | Yano et al. |
| 2012/0132381 A1 | 5/2012 | Hentze et al. |
| 2014/0079931 A1 | 3/2014 | Berglund et al. |
| 2015/0234098 A1 | 8/2015 | Lofftus et al. |
| 2016/0010279 A1 | 1/2016 | Hu et al. |
| 2016/0130370 A1 | 5/2016 | Meredith, III et al. |

FOREIGN PATENT DOCUMENTS

| | | | |
|---|---|---|---|
| CN | 101942102 A | | 1/2011 |
| CN | 102703092 A | | 10/2012 |
| CN | 102899949 A | | 1/2013 |
| CN | 103421203 A | | 12/2013 |
| CN | 107936433 A | | 4/2018 |
| EP | 1512729 A1 | | 3/2005 |
| EP | 2 684 898 A1 | | 1/2014 |
| JP | 2009-299043 A | | 12/2009 |
| JP | 2010-107336 A | | 5/2010 |
| JP | 2014163028 A | * | 9/2014 |
| WO | WO 99/03928 A1 | | 1/1999 |
| WO | WO 2010/092239 A1 | | 8/2010 |
| WO | WO 2010/124396 A1 | | 11/2010 |
| WO | WO 2010/142846 A1 | | 12/2010 |
| WO | WO 2011/059398 A1 | | 5/2011 |
| WO | WO 2011/070923 A1 | | 6/2011 |
| WO | WO 2013/121086 A1 | | 8/2013 |
| WO | WO 2017/127362 A1 | | 7/2017 |

OTHER PUBLICATIONS

Search Report of the FIPO for FI 20175855 dated Mar. 14, 2018.
International Preliminary Report on Patentability for PCT/EP2018/076186 dated Mar. 31, 2020.
Wang et al., Self-assembled clay films with a platelet-void multilayered nanostructure and flame-blocking properties. Sci Rep. 2013;3:2621. doi: 10.1038/srep02621.
International Search Report and Written Opinion mailed Dec. 17, 2018, for Application No. PCT/EP2018/076186.
Bettini et al., Food-grade TiO(2) impairs intestinal and systemic immune homeostasis, initiates. Preneoplastic lesions and promotes aberrant crypt development in the rat colon. Sci Rep. Jan. 20, 2017;7:40373(1-13). doi: 10.1038/srep40373.
Caixeiro et al., Disordered Cellulose-Based Nanostructures for Enhanced Light Scattering. ACS Appl Mater Interfaces. Mar. 8, 2017;9(9):7885-7890. doi: 10.1021/acsami.6b15986. Epub Feb. 22, 2017.
Fang et al., Novel nanostructured paper with ultrahigh transparency and ultrahigh haze for solar cells. Nano Lett. Feb. 12, 2014;14(2):765-73. doi: 10.1021/nl404101p. Epub Jan. 13, 2014.
Henriksson et al., Cellulose nanopaper structures of high toughness. Biomacromolecules. Jun. 2008;9(6):1579-85. doi: 10.1021/bm800038n. Epub May 23, 2008.
Toivonen et al., Ambient-dried cellulose aerogel membranes with high tensile strength and their use for aerosol collection and templates for transparent, flexible devices. Adv Funct Mater. Jan. 1, 2015;25(42):6618-25.
Office Action for CN Application No. 201880062417.7 dated Feb. 27, 2022.
Office Action for JP Application No. 2020-537874 dated Sep. 20, 2022.
Barthelemy et al., A Lévy flight for light. Nature. May 22, 2008;453(7194):495-8. doi: 10.1038/nature06948.
Yang et al., Cellulose-Based Scattering Enhancers for Light Management Applications. ACS Nano. May 24, 2022;16(5):7373-7379. doi: 10.1021/acsnano.1c09198. Epub Apr. 27, 2022. Supporting Information.

* cited by examiner

Fig. 3
Fig. 3A
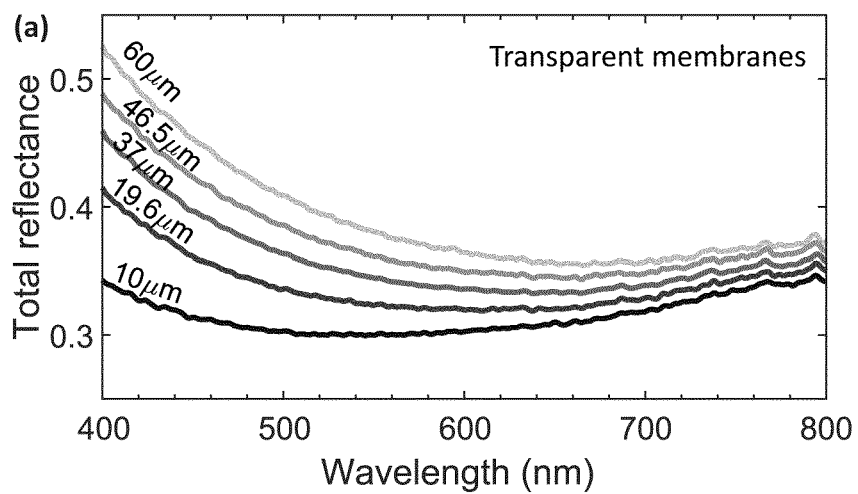
Fig. 3B
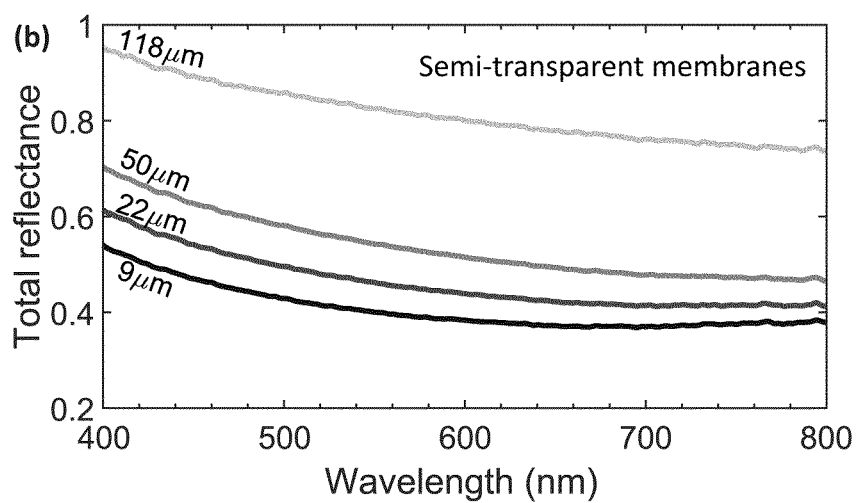

HIGHLY SCATTERING POROUS MATERIAL BASED ON FIBRILLAR, ELONGATED, OR DISK-LIKE PARTICLES

RELATED APPLICATION

The present case is a national stage filing under 35 U.S.C. § 371 of international PCT application, PCT/EP2018/076186, filed Sep. 26, 2018, which claims priority to, and the benefit of, Finnish Patent Application, 20175855, filed on Sep. 26, 2017, the entire contents of each of which are hereby incorporated by reference.

BACKGROUND OF THE INVENTION

Field of the Invention

The present invention concerns a porous material based on fibrillar, elongated, or disk-like particles, a process for the preparation of such a material, maintaining its porosity, as well as the use of such a material.

Description of Related Art

Cellulose nanofibrils (CNF), also denoted as cellulose nanofibres, nanofibrillated cellulose (NFC), or microfibrillated cellulose (MFC), have drawn much attention in recent years due to their attractive combination of high mechanical properties and tailored opacity (from transparent to translucent), renewability, availability, biocompatibility, and thus their potential for use as advanced functional materials. The versatility of CNF has been demonstrated in forming a myriad of versatile materials including transparent and water-resistant nanopapers, nanostructured foams, cell-growth supporting hydrogels, mechanically robust and transparent aerogels and membranes, as well as strong and functional fibres.

Transparency is often attempted and highlighted in CNF-based materials, as this is easily achievable using conventional processes resulting in small fibril sizes and compact films. Also a high degree of porosity has been achieved.

For example, Fang Z et al. (2014) have described the use of CNFs for transparent films with high haze, which comes from their scattering properties.

Caixeiro S. et al. (2017), in turn, describe the use of cellulose nanocrystals (different from CNF) to produce a highly scattering material which is based on inverse-spherical elements. Such materials based on CNCs are, however, typically to brittle for many purposes.

Propagation of light through a medium with a varying refractive index leads to scattering, and this scattering becomes most efficient when these variations in refractive index occur in structures with sizes comparable to the wavelength of light. Strong scattering is a highly sought after property for sustainable cellulose-based technologies.

For instance, strong scattering helps improve the colour yield for dyed fibres, which is known to be difficult to achieve for nanofibres as compared to common macrofibres. Further, paper whiteness is often enhanced using additives, which, however, can cause allergic reactions and negative health effects, and in large doses may have a negative impact on the environment.

For example, titanium dioxide nanoparticles have been found to have negative health effects on rats when added to food (see Bettini S. et al. (2017)).

Therefore, there is a need for replacing such additives, both in paper and in other products, particularly edible and dermatological products. Highly scattering materials providing high diffused reflectivity in short thickness are highly desirable. Materials, where anomalous diffusion is observed, provide this desired optical property. The phenomenon has been described previously (Barthelemy et al Nature 453, 495-498, (2008)). However, it has not been foreseen that such properties can be achieved in edible or biosafe materials, in particular organic materials, even more particularly in celluloses.

In nanofibres, the optical characteristics can be affected by modifying the morphology of the fibres (i.e. diameter of the fibres, their packing into larger aggregates, and the density and porosity of the macroscopic structure), since this defines how the light is transmitted through the material and scattered by the fibres.

One possibility is to use the nanofibrils in forming aerogels, which are porous and low density solid materials with a high specific surface area, exhibiting beneficial mechanical, optical and gas transport properties, as well as renewability, availability and biocompatibility. However, inorganic aerogels, in particular, such as silica aerogels, typically suffer from brittleness.

The publication of Toivonen et al. (Adv. Funct. Mater. 2015; 25: 6618-6626) describes the fabrication of such high transparency CNF aerogel membranes, forming fibrils having a diameter of 5-20 nm. However, as mentioned, these aerogels are transparent in contrast to those described below.

Materials with high scattering levels can also be utilized in order to achieve, e.g. opacity (or whiteness), which is a desired optical property in countless industrial products, e.g. toothpaste and white paint. In these materials high opacities are typically achieved by using titanium derivatives, such as titanium dioxide ($TiO_2$), or zinc oxide (ZnO). These particles act as separate light scatterers, thereby enhancing the whiteness of the material. However, as mentioned above, these separate scatterers have been found to have negative health impacts.

Publication US2015234098 describes a lightweight article comprising an opacifying layer that is capable of blocking visible-range electromagnetic radiation. The material contains porous particles (of the size 2-50 μm) and a separate opacifying colorant that absorbs the predetermined electromagnetic radiation.

However, additives typically cause materials to become more brittle, and can cause toxicity as well as environmental hazards, therefore the concentrations of these additives must be kept low, and preferably avoided. If no additives are used, the opacity of the material decreases. Hence, to achieve a satisfactory level of opacity, a larger amount of materials is required. That is, a larger thickness is needed to obtain a uniform covering.

Furthermore, adding fibrillar strong nanomaterials, such as CNF, can make the materials mechanically stronger and tougher.

US2012/0132381 A1 discusses a nano-cellulose containing material for use in paper. The materials are made by simple dispersing cellulose in a solvent and subsequently filtering and drying the cellulose to form a film. The film is thick, 139 μm to 190 μm, and provides modest opacity.

Thereby there is an on-going need for more efficient, thin (less than 10 micrometers), strong and non-toxic opaque materials.

SUMMARY OF THE INVENTION

The present invention is defined by the features of the independent claims. Some specific embodiments are defined in the dependent claims.

The present invention is based on the finding that opacity or whiteness can be provided by creating an appropriately porous structure from a biologically and environmentally benign material, such as CNF. In fact, maximal scattering in the sense of % of backscattered light/thickness of the material can be achieved by optimisation of particles in terms of size, refractive index, and filling fraction (i.e. spatial arrangement). When using the materials described herein, such as the fibrous or sheet-like particles, it is the spatial distribution and size of the particles that are to be optimized, while maintaining a sufficiently high contrast in refractive index between the particulates and the embedding medium. Both anisotropic and isotropic materials can be used.

According to a first aspect of the present invention, there is provided a highly scattering material based on fibrillar, elongated, or disk-like particles.

According to a second aspect of the invention, there is provided a material, based on fibrillar, elongated, or disk-like particles, that is capable of forming a highly opaque membrane, coating or film, while maintaining a relatively low film thickness.

According to a third aspect, there is provided a process for preparing such a material.

Opacity, achieved with a thin structure, can be enhanced by altering the way light propagates inside the scattering medium. The total transmission, T, of a material of thickness, L, can be described with the equation $T=1/(1-A*L^{\alpha/2})$, where A and $\alpha$ are constants. In a typical scattering medium, propagation of light occurs by normal diffusion, and then the constant $\alpha=2$. However, when the microstructure of the scattering medium leads to a distribution of step lengths (i.e. distances between scattering events) that has a heavy tail (i.e. very long steps become non-negligibly probable), the constant $\alpha<2$, and the propagation of light occurs by super-diffusion. More broadly, when $\alpha \neq 2$, the diffusion is called anomalous diffusion. Two structures that may lead to anomalous diffusion and superdiffusion are schematically illustrated in FIG. 8. The practical relevance of the constant $\alpha$ is that for very small thicknesses, the total transmission may become lower when the value of $\alpha$ is reduced, assuming that the constant A remains the same. In essence, this means that the total reflectivity of the thin coating will be enhanced.

According to a fourth aspect, there is provided a new use of such a material as a coating or protective film, typically by applying the material in powder form, e.g. by pad printing, spraying or electrostatic deposition.

According to a fifth aspect, there is provided a new use of the above described material as a scattering enhancing component, embedded in a liquid or solid formulation, e.g. by dispersing the material in powder form in a given solvent, water, or an emulsion system, from which it can be further applied to a desired product.

Thus, the present invention concerns a material based on fibrillar, elongated, or disk-like particles, a process for producing such a material, and the use of the material.

The material of the invention scatters light very efficiently and thus appears white, or frosted, even as a very thin membrane. The unconventionally strong response is the result of the appropriately dense (with an optimal density in terms of scattering efficiency) porous random network of the material.

Regarding the density, it can be said that if the density is too high, the scattering is suppressed, and if the density is too low, the scattering is no longer enhanced significantly and the thickness/volume required to achieve an opaque appearance increases.

The material can be constructed from fibrillar nanomaterials with different diameters, or materials having diameters from 10 nm up to 1000 nm, e.g. cellulose nanofibrils (CNF).

Several advantages are achieved using the present invention. Among others, the invention enables the use of lower thickness of opacifying surface elements, such as paints and coatings, thereby reducing the total costs of their applications, and forms a lower percentage by weight (or by volume) of the overall product. This also has a positive effect on e.g. logistics.

The material of the invention can achieve opaque coatings with a thickness as low as 3 micrometers, if there is no solid support, depending on the substrate properties. This is as much as 20-100 times thinner than the coatings of the current state of art. Furthermore, the material is environmentally friendly and lends itself to applications where non-toxicity is critical, such as paper products, as well as cosmetic or edible products, the latter including medicines, food and topically applicable formulations.

The material of the invention can achieve opaque coating at the said low thicknesses partially due to the microstructure of the material leading to propagation of light to occur by superdiffusion or anomalous diffusion of light inside the material.

Particularly in case of the starting materials that are based on cellulose, the manufacturing process of the products is relatively inexpensive, particularly compared to the use of various additives, and sustainable. Moreover, the final products are biocompatible. Their sustainability is further increased by the fact that they are lightweight and can be used in small amounts.

The process for preparing the material has several advantages over the slow and costly freeze- or supercritical drying method that typically is used for preparing aerogels. Instead of these drying conditions, the present method can be carried out in ambient conditions.

DETAILED DESCRIPTION OF THE PREFERRED EMBODIMENTS OF THE INVENTION

Figure 1:
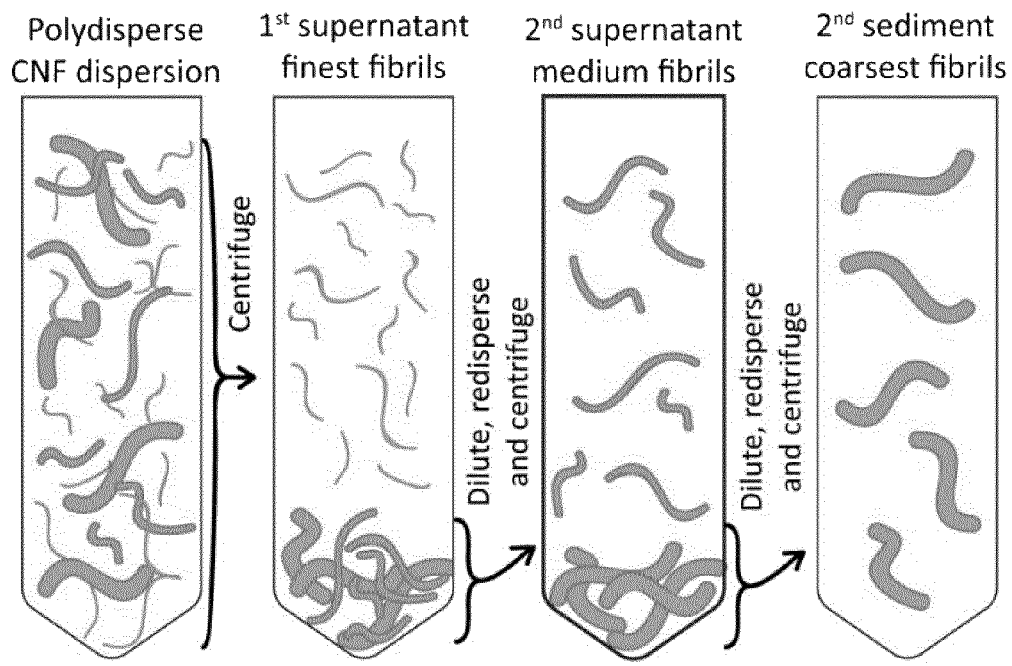
FIG. 1 is a schematic illustration of the preparation procedure of the fractioned CNF dispersions by differential centrifugation.

Definitions:
  The present invention is based on a material formed of "colloidal particles", comprising structural units having at least one dimension ranging from 1 nm to 1 μm. Their shape can vary widely, from rod-like, fibrillar, spherical, plates and sheets, to even more complicated shapes, but are typically formed of fibrillar, elongated, disk-like, rod-like or plate-like particles, such as particles shaped as fibrils or sheets or the like. Also the composition of the colloidal structural units can very widely, from organic to inorganic materials to composites, where the preference in the present context is sustainable materials, still more preferably biologically safe materials, most preferably edible materials. The colloidal structural units can assemble into branched, nonbranched fibrillar adducts or sheets, relevant for the present invention, depending on the processing and materials selection.
  The term "edible" is intended to cover materials that have been approved by national or international organizations, such as materials that have been listed in the Annex of Commission Regulation (EU) No 1130/2011.
  Another term used for the material of the invention is material based on fibrillar, elongated, or disk-like particles. In this context, the term "based on fibrillar, or elongated particles" is intended to cover all materials formed of 40% or more branched or non-branched fibrils, or colloids as described above or the like calculated from the weight of the solids of the material. Likewise, the term "based on disk-like particles" is intended to cover all materials formed of 40% or more sheet-like structures calculated from the solids of the material. When a lower scattering is sufficient, a lower amount of fibrils in the material can also be sufficient.
  However, in the materials of the present invention, it is preferred that 90% or more of the solids of the starting material is in the form of nano fibres, nanofibrils or other nanostructures, which in the present context is intended to cover structures having a diameter, or thickness, of 500 nm or less. The remaining part of the solids preferably includes at least some particles having a diameter of up to 1000 nm.
  The term "opaque" or "opacity" is in the present context intended to define a visual quality of the materials of the present invention, meaning the opposite of "transparent". In the following, the materials of the invention will be referred to as "transparent", "semi-transparent", and "white" or "opaque", corresponding to their appearances.
  However, in practice, the meanings of these terms are more complex, as several grades of transparency or opacity exist. Typically, the present materials can visibly be determined to have significantly higher opacities than materials of the prior art generally considered to be transparent.
  The materials of the invention are considered to be "porous", or to be formed of a "macroporous fibre network", a "mesoporous fibre network", or a combination of these. Such a network is typically in the form of a film or membrane, although porous particles in the form of a powder also belong to the scope of the invention. In this context, "porous" refers to a structure that is partially filled by solid material and partially by a non-solid material, such as a gas.

The present invention thus concerns a method for manufacturing a porous material in the form of a film or a powder, based on fibrillar, elongated or disc-like particles, wherein an aqueous dispersion of the particles is filtered and the desired fibril fraction(s) are transferred into a volatile solvent, such as octane, e.g. by solvent exchange, followed by ambient drying. The product can either be recovered as a powder, or applied into a layer to form a film.

The method includes the step of providing a starting material, which is based on fibrillar, elongated, or disk-like particles, or other similar particle structures, having a diameter or thickness of 1000 nm or less.

Based on one option, an untreated raw material, with a wide distribution of fibril diameters, can be fractioned, typically by a sequential centrifugation procedure, e.g. according to the procedure illustrated in FIG. 1. This procedure results in dispersions of varying transparency, where the scattering is weakest for the dispersion with the finest fibrils and strongest for the dispersion with the coarsest fibrils. The scattering strength can be then tuned on demand by choosing the dispersion with fibrils of an appropriate diameter distribution.

The trend in transparency/opacity of the dispersions is due to increased scattering efficiency and distances between individual particles, which is a result of increasing particle sizes. Also the pores themselves, in the porous material of the invention, can act as scattering centres. Due to their pore-forming ability, larger diameters than in conventional transparent products are therefore preferred, but smaller than what are typically utilized in pulp materials, such as paper. An optimum in scattering power has been found for structures based on fibrils or other similar particles with diameters in the range of 150 to 500 nm, although a sufficiently strong scattering power is obtained with a diameter range of 10 to 1000 nm.

The present opaque coatings have typically been achieved using materials microstructures leading to propagation of light to occur by superdiffusion or anomalous diffusion of light inside the material.

Optionally, one or more further components, in the form of polymers or monomers, can also be added, either to the starting material or to the formed dispersion.

After obtaining a dispersion containing the desired fraction(s) of particles, and following an optional cross-linking step, a drying step is typically carried out. The drying can be achieved in ambient conditions, or in vacuum or at lowered pressure, or at high or low temperatures. Even a freeze drying procedure can be used.

According to an embodiment of the invention, in order to prepare porous membranes from the dispersions, the dispersions are filtered into a wet gel cake, typically by vacuum filtration. Preferably, the filtering is followed by a solvent exchange from water to e.g. octane, optionally using one or more intermediate solvents and more than one solvent exchange step. From this solvent solution, the gels are slowly dried in ambient conditions.

For the membranes, octane is a preferred solvent due to the thus achieved lower surface tension, and stronger bonding at the intersections of the fibrils, as the hydrogen bonds between the fibrils are no longer in competition with water. This causes a decreased tendency of the formed porous membranes to crumple or wrinkle and become compact upon drying. Other options include various non-polar volatile organic solvents, such as hexane, benzene and toluene.

For the powders, a different drying procedure can be used. For example, spray-drying from water or another solvent, typically being a non-polar solvent, can be used. In the case of such powders, it is also preferred to use fibrils having a diameter of 10-1000 nm, more preferably 150-500 nm, formed for example by enzymatic hydrolyzation and mild mechanical disintegration.

The densities of the thus obtained materials are typically in the range between 400 and 950 kg m$^{-3}$ and no systematic differences between the membranes are observed within these density limits.

The porosity, or filling fraction, and the random distribution of fibrils of the materials is essential for efficient broad band optical scattering. In a compact film or other structure, optical crowding would occur if the scattering centers would be placed too close together.

There is a microstructural difference of the white membranes when compared to the transparent and semi-transparent membranes, which corresponds to the pore width distribution, which in turn leads to different porosities. The specific surface areas of the transparent, semi-transparent and white membranes have, based on one experiment, been found to be about 190, 175 and 122 m$^2$/g, respectively.

Thus, the materials of the present invention typically have a specific surface area of 150 m$^2$/g or below, preferably within the range of 100 to 140 m$^2$/g.

According to an embodiment of the invention, colorants or aromatics can be added to change the colour, taste or smell of the material. Due to the porosity of the material of the invention, these can be added e.g. by simply absorbing. The amount of these additives is, however, required to be small to prevent any remarkable change in the characteristics of the material, due to for example the filling of the pores.

The present invention also concerns a porous fibril-based material in the form of a network, such as a material prepared according to the above described method, shaped as a film or as a powder, and comprising a fibrillar solid, and air or another similar gaseous agent to fill the pores, whereby the material contains 20-80% by volume of solids, preferably with a maximum of 70% by volume of solid material.

According to an embodiment, the material is formed of a network of cross-linked fibrils. Crosslinking will have several advantages, such as improving the strength of the final product. Further, when the crosslinking takes place before drying (i.e. before evaporating the solvent), the product has a higher resistance to shrinkage, collapse and compactification, and hence will maintain a higher porosity and opacity.

The aim of the invention is to achieve maximal scattering, whereby the invention is focused on an optimization of particles in terms of size, refractive index, and filling fraction, as well as membrane thickness. For example, when using a membrane according to the present invention, a thickness of one tenth of the thickness of paper is sufficient to cause a comparable amount of scattering to that of paper. In other words, the membrane of the invention has a light scattering that is 10× stronger than for conventional paper.

Further, to achieve the desired product characteristics mentioned above, at least a fraction of the fibrils of the fibrillar solid are selected from those having a diameter within a distribution in the range 10-1000 nm, polydispersity is needed for the effect; it is preferred for this fraction of the particles to have a diameter within the range 150-500 nm.

Pores are formed between the particles, and a suitable agent can be used to fill the pores and provide a more long-lasting porosity. This agent is preferably air, but can also be selected from any other material with low refractive index.

According to a preferred embodiment of the invention, the fibrillary solid is in the form of nanofibrils or nanocrystals. Nanofibrils are typically formed of longer structures, which thereby enable stronger interlinks in the structure, due to having a larger number of contact points/intersections between each other, thereby providing mechanically stronger materials.

A preferred fibrillary material is cellulose, particularly nanocellulose. Also cellulose fines resulting from cellulose pulping may be used, or bacterial cellulose. For example, bleached birch pulp has been found to provide the desired type of fibrils.

Figure 9:
FIG. 9 is a photograph of a bright white coating formed by drying a water emulsion with a wax formulation (1-octadecanol, Tween 80, and chitosan) solidified to flat platelets assembled into droplets acting as scatterers.
Figure 10:
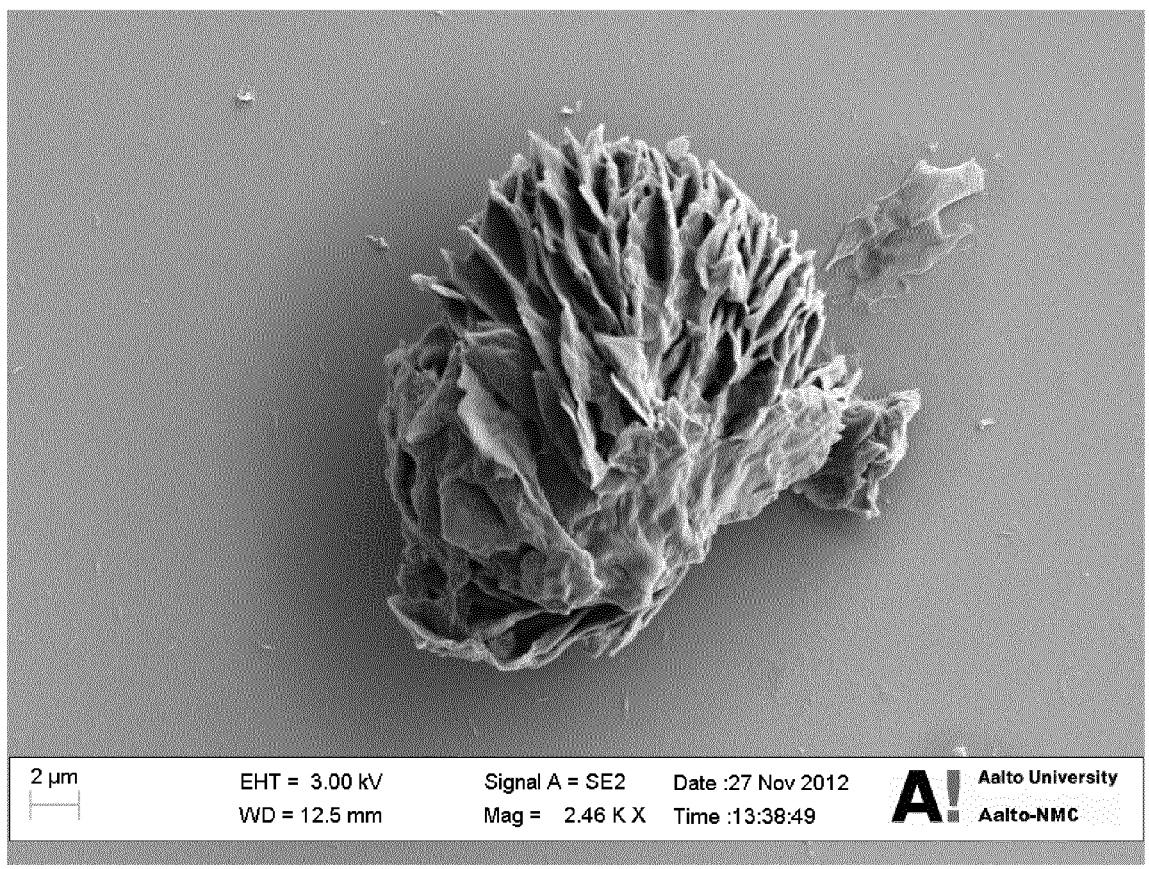
FIG. 10 is a scanning electron micrograph (SEM) of a wax droplet assembled from flat platelets mostly composed of 1-octadecanol.

According to a further embodiment of the invention, nanofibrillated chitin is used as raw material, due to its similarities to cellulose nanofibrils. Other options comprise keratine, or small molecules which solidifiy into fibrillar structures, such as some waxes, fats and sugars. For example, FIG. 9 shows a film formed by drying an emulsion of droplets assembled of solid wax platelets, the structure of which is shown in an SEM image in FIG. 10. It is, however, particularly preferred to select a raw material that is non-toxic, most suitably even edible.

Typically, the desired end-use of the product will have an effect on the further requirements for the starting material. For example, when using a cellulose-based raw-material, the presence of lignin will provide a brownish product. Thereby, in case a white colour is desired, the lignin is typically removed, unless the scattering by the structure is sufficiently efficient to reduce absorption to negligible levels. Also the lack of toxicity, taste, or allergenic activity, required in some final applications, has an effect on the choice of raw-material.

According to one embodiment of the present invention, the product of the invention is provided in the form of a porous membrane or coating.

According to another embodiment, the product is provided in the form of a powder. The powder may be fabricated using the same methods as with aerogel but the concentration of solvent needs to be lower or lowered, e.g. by spray drying.

In conclusion, the present invention provides a cellulose-based system in which it is possible to tune the light transport properties by fractionation of the starting material. A high degree of scattering strength has been observed despite the low refractive index contrast between the CNFs and air, thanks to the optimized morphology and spatial distribution of the scattering centres.

A particularly preferred product of the present invention is in the form of a membrane, where the ratio of light scattering/membrane thickness has been optimized, i.e. maximized.

As described above, another option is to provide the material in the form of a powder or a powder coating.

The above product can be produced either by using the described method, or simply by mixing particles of different sizes to provide the desired material, formed of the desired particles.

Possible final end-uses of the material of the invention include the use as, or as a part of, colorants or whiteness enhancers, e.g. in paints or as protective films. In conjunction with the use of pigments and other colorants, the material of the invention can also be used as an enhancer of other colours than only white.

Food-, medicament- and cosmetics-related uses are preferred alternatives, as well as use in paper, since the product of the invention is non-toxic and even edible.

Furthermore, the material is capable of providing a white colour, and is inert in the sense of smell and taste, whereby it can be used, e.g. as a replacement for the $TiO_2$ films commonly used in medicaments. Due to the porosity of the present materials, and to the fact that the porosity and strength of the material can be affected by adding various additives, these materials can also cause a change in the release rate of the active agents of these medicaments.

The light scattering characteristics of the product are highly suitable for these uses, as well as the small amounts required.

Another alternative is the use of the material in vehicle paints, if appropriately hydrophobized or protected from the effect of humidity. Particularly, this is an alternative if the material appropriately chemically modified by for example hydrophobization. For aircrafts, the use of such water-repellants would also result in a decreased risk of icing. In these vehicle paints, functionalized fibrils could be considered, such as fluorinated fibrils, since such materials would further decrease the water absorbance.

A further area of application of the material of the invention is as a light-harvesting component in solar cells. The material is suitable for harvesting of light as an anisotropic scattering medium. It is possible for light to have a preferred direction of propagation along the plane of the material, rather than across it, if the scattering events are weaker or more sparsely spaced for light propagating in the plane of the material. Thus, in e.g. a solar panel, the material could increase the efficiency of the solar cells.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In this description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The following non-limiting examples are intended merely to illustrate the advantages obtained with the embodiments of the present invention.

EXAMPLES

Example 1

Manufacturing and Analysis of Porous CNF Membranes
Materials:

CNF was prepared from never dried birch pulp by disintegrating the pulp 6 times through a fluidizer (Microfluidics Corp., Newton, MA, USA) leaving a hydrogel with a consistency of approximately 1.5 wt. %.
Fractioning of the CNF Dispersion by Sequential Centrifugation:

The hydrogel was diluted to 0.3 wt. % by adding deionized water followed by vigorous stirring and homogenization with a high-shear homogenizer (Ultra Turrax T25 basic IKA Labortechnik) for 30 min at 11,000 rpm. After dilution and homogenization the original CNF dispersion was centrifuged as illustrated in FIG. 1, whereby first a centrifugation at 5,000 g-forces was carried out and the supernatant collected. The CNF in this first fraction are in the following called the "finest fibrils".

Subsequently, the sediment was repeatedly diluted, redispersed and centrifuged again as described above, until the bluish hue resulting from scattering of light by the small dispersed fibrils in the supernatant was no longer observed. Then, the same process was repeated with a lower centrifugal speed of 4,000 g-forces and the supernatant was again collected. The CNF in this second fraction are in the following called the "medium fibrils".

Lastly, when the supernatant displayed no bluish hue resulting from scattering of light, the sediment was collected, diluted and redispersed. The CNF in this last fraction are called the "coarsest fibrils" in the text. The sequential centrifugation process resulted in dispersions of varying transparency where the scattering was weakest for the first dispersion and strongest for the final one.

Preparation of Mesoporous CNF Membranes:

Subsequently, the porous membranes were prepared. A given amount of one of the three fractioned CNF dispersions was vacuum filtered on a hydrophilic polyvinylidene fluoride filter membrane (0.45 µm, GVWP, Millipore) until a wet gel-cake was formed and no vibration of a water layer was observed when the filtering apparatus was sharply tapped. The filtration step was completed typically in 15 minutes. The filter and gel-cake were carefully transferred to a glass Petri dish and ethanol was pipetted to the edge of the filter paper before drying of the gel-cake occurred, while avoiding excessive mechanical disturbance to the gel-cake, until both were fully immersed in ethanol. After an approximate 5 min soak in ethanol, the filter and gel-cake were inverted onto a smooth polytetrafluoroethylene (PTFE) sheet leaving the gel-cake resting on the PTFE and the filter membrane on top. A small amount of ethanol was pipetted on the gel-cake to avoid drying and the filter membrane was carefully peeled from the gel-cake and discarded. The gel-cake was covered with 2-propanol for typically 5 minutes to exchange the remaining water and ethanol in the gel-cake to 2-propanol after which the used 2-propanol was discarded and new was added. This was repeated three times. After solvent exchange to 2-propanol, the same procedure was repeated using octane. After the gel-cake was soaked three times in octane, the excess octane was discarded and the gel-cake was left to dry slowly on the PTFE sheet in ambient conditions while partially covered with a glass Petri dish. During all soaking steps, the gel-cake and solvent were covered with an inverted Petri dish to avoid drying.

Compact CNF films, as opposed to porous membranes, were prepared similarly as the membranes with the difference that after peeling of the filter membrane the solvent was exchanged back to water. In this case the gel-cake was dried slowly from water on the PTFE sheet.

Thickness Measurement:

The thicknesses of the films were measured with a film thickness measurement set-up composed of a displacement sensor (LGF-0110L-B, Mitutoyo), digital reader (EH-10P, Mitutoyo) and a measuring table with support for sensor (215-514 comparator stand, Mitutoyo).

AFM Characterization of the Fractioned CNF:

The morphologies of the fractioned CNFs were investigated using a Dimension 5000 scanning probe microscope with NanoScope V controller (Veeco). The samples were prepared by first diluting a dispersion of the fractioned CNF to approximately 0.001 wt. % with deionized water and pipetted onto a clean microscope glass slide. The excess dispersion was removed by turning the glass slide vertical. Subsequently, the samples were dried at room temperature for 24 hours prior to measurement. The images were scanned in tapping mode in air using silicon cantilevers (NSC15/AIBS) delivered by MicroMash (Tallinn, Estonia). The data was postprocessed in order to flatten substrate background and remove streaks from scanning artefacts.

Figure 2:
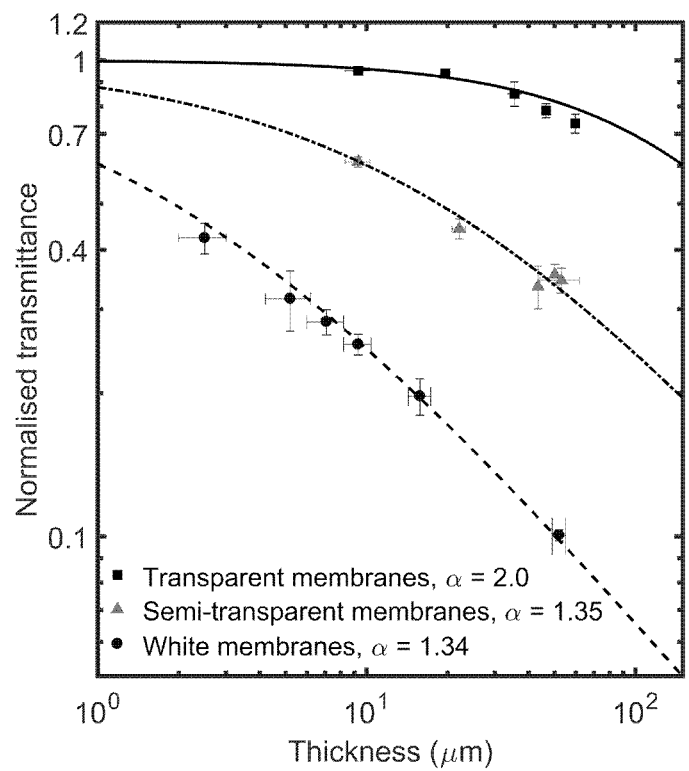
FIG. 2 is a graph showing the total transmission at 600 nm as a function of sample thickness, where the data series have been fitted by least-square regression (lines), where the thin (10-30 μm) transparent membranes (squares) transmit about 90% of the incident light, an increased inhomogeneity (triangles) is coupled with a more steep decay of the transmission (still transmitting approximately 65% of the light at a thickness 10 μm), and where the most opaque films (circles) transmit only 40% of the light even at a thickness of approximately 3 μm.

Total Transmittance Measurements:

The samples were illuminated using a Xenon lamp Ocean Optics HPX-2000 coupled into an optical fibre (Thorlabs FC-UV100-2-SR). The transmitted light was collected by an integrating sphere (Labsphere) and the signal was acquired by a spectrometer Avantes HS2048. The integrating time was set to 1 s and 10 spectra were acquired for each sample of different thickness and averaged together. The results are shown in FIG. 2.

Figure 3C:
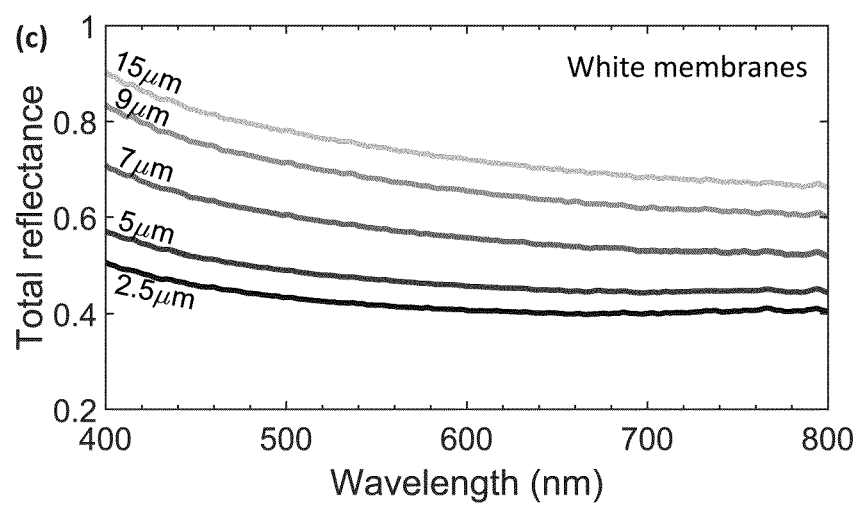
FIG. 3 is a series of graphs showing the measured reflectance for the (A) transparent, (B) semi-transparent, and (C) white membranes.

In addition, the reflectance values were measured, for the transparent, semi-transparent, and white membranes. The measurements were normalised with respect to a standard white diffuser and collected with numerical aperture (NA) 0.95. The results are shown in FIG. 3 (A-C). The thickness of the films is reported in the legend.

Figure 4:
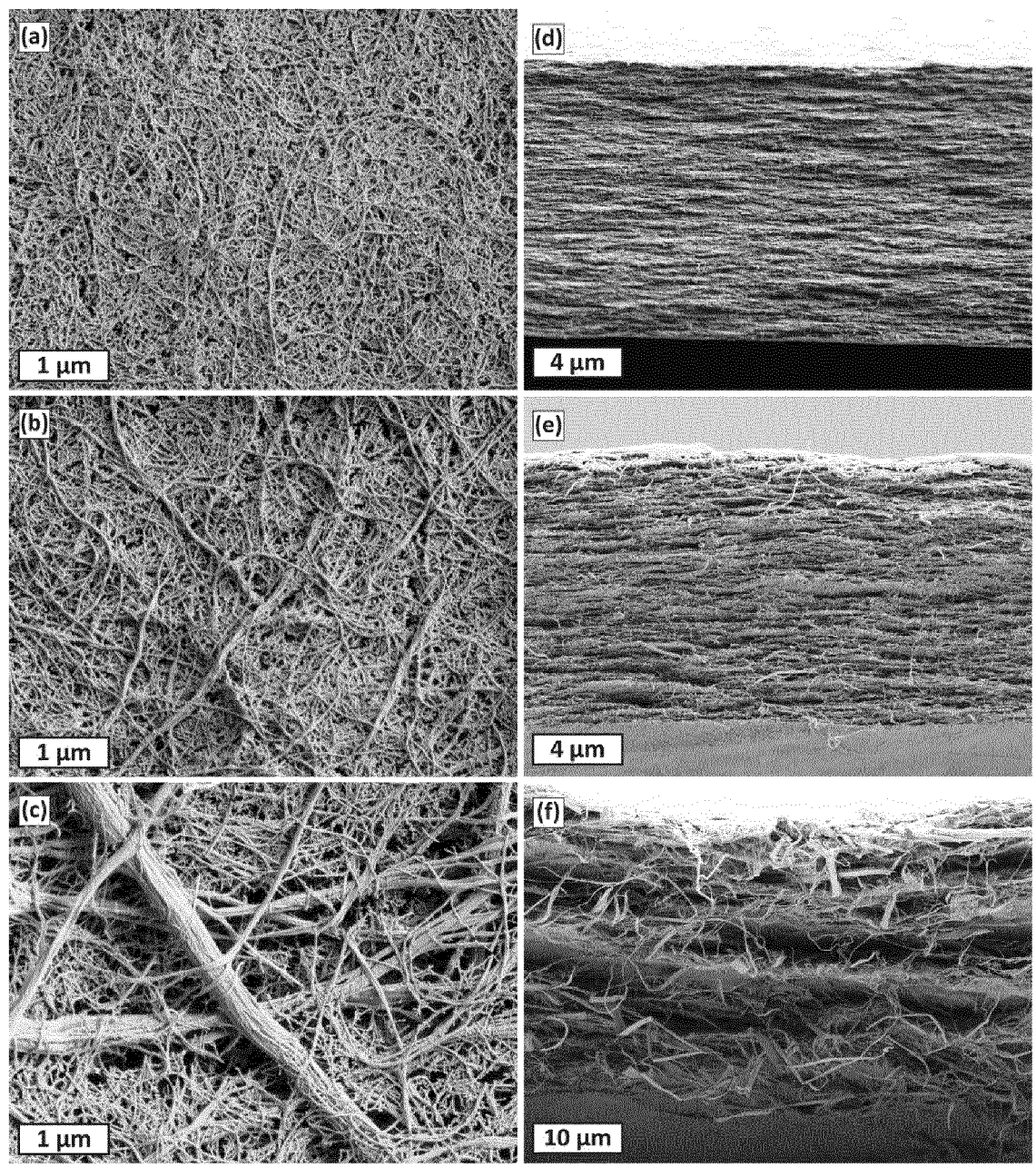
FIG. 4 is a series of SEM micrographs of top surfaces of membranes (a-c) and their corresponding cross-sectional fracture surfaces (d-f). The micrographs are of the (a,d) transparent, (b,e) semi-transparent, and (c,f) white membranes.

SEM Characterization:

Dry porous CNF membranes were imaged in SEM from the top and from the cross-sectional view. For imaging from the top small pieces of membranes were cut and attached to an aluminium SEM stub with carbon tape. An approximately 2 nm thick gold film was sputtered (Emitech K100X). Imaging was carried out with a Zeiss Sigma VP scanning electron microscope at 1-2 kV acceleration voltage. The results are shown in FIG. 4.

Figure 5:
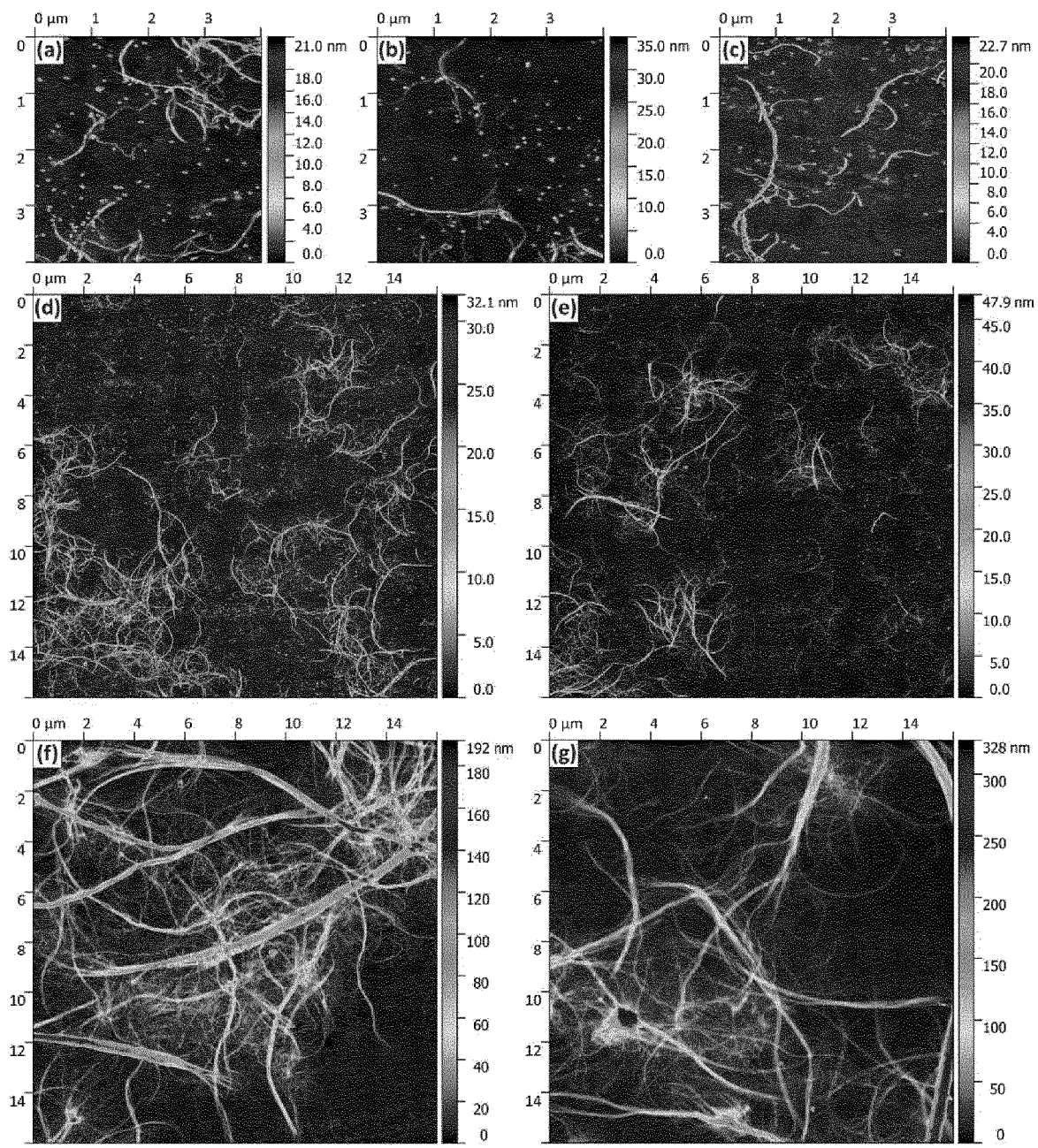
FIG. 5 is a series of AFM micrographs of (a,b,c) finest, (d,e) medium, and (f,g) coarsest fibrils.

The particles as such were also subjected to imaging before forming the membranes. For this purpose, a series of AFM micrographs were obtained, as shown in FIG. 5.

Figure 6:
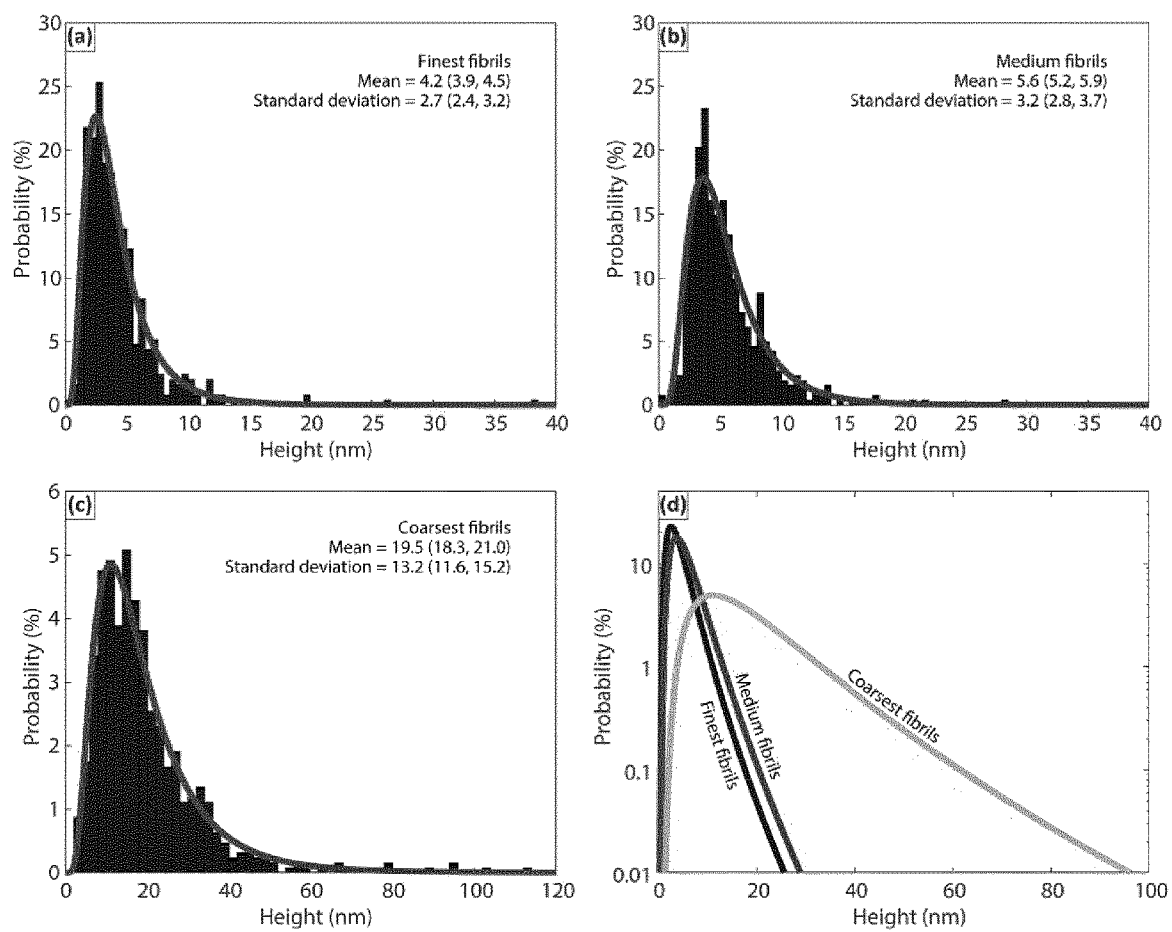
FIG. 6 shows fibril diameter histograms and fitted log-normal models of (a) finest, (b) medium, and (c) coarsest fibrils, with a comparison of the fitted log-normal models shown in (d) with the vertical axis as logarithmic to highlight the presence of a small amount of significantly thicker fibrils.

Fibre diameter histograms are shown in FIG. 6, and the parameters are provided in the following Table 1:

| Parameter | Finest fibrils | Medium fibrils | Coarsest fibrils |
|---|---|---|---|
| Mean | 4.2 nm | 5.6 nm | 19.5 nm |
| Standard deviation | 2.7 nm | 3.2 nm | 12.7 nm |
| µ | 1.3 | 1.6 | 2.3 |
| µ- 95% confidence interval | (1.2, 1.3) | (1.5, 1.6) | (2.3, 2.4) |
| σ | 0.59 | 0.54 | 0.77 |
| σ-95% confidence interval | (0.56, 0.63) | (0.51, 0.57) | (0.73, 0.82) |

Specific Surface Area and Pore Size Distribution by Nitrogen Adsorption:

N2 physisorption data was measured at least once for each of three identically prepared CNF membranes with a Micromeritics TriStar II automated system. The samples, 10-20 mg each, were stabilized for 1 h under vacuum in their measurement vessels before zeroing the transducers and running free-space measurements with helium both at ambient and measurement temperature (77 K). The adsorption isotherm was collected by increasing the relative pressure from 0 to 0.99 and back while recording over 100 data points. The Brunauer-Emmett-Teller specific surface area analysis (BET) was carried out for a relative N2 vapour pressure of 0.05-0.30. Pore size distribution was determined according to Barrett-Joyner-Halenda (BJH) method from the full adsorption isotherm range.

Figure 7:
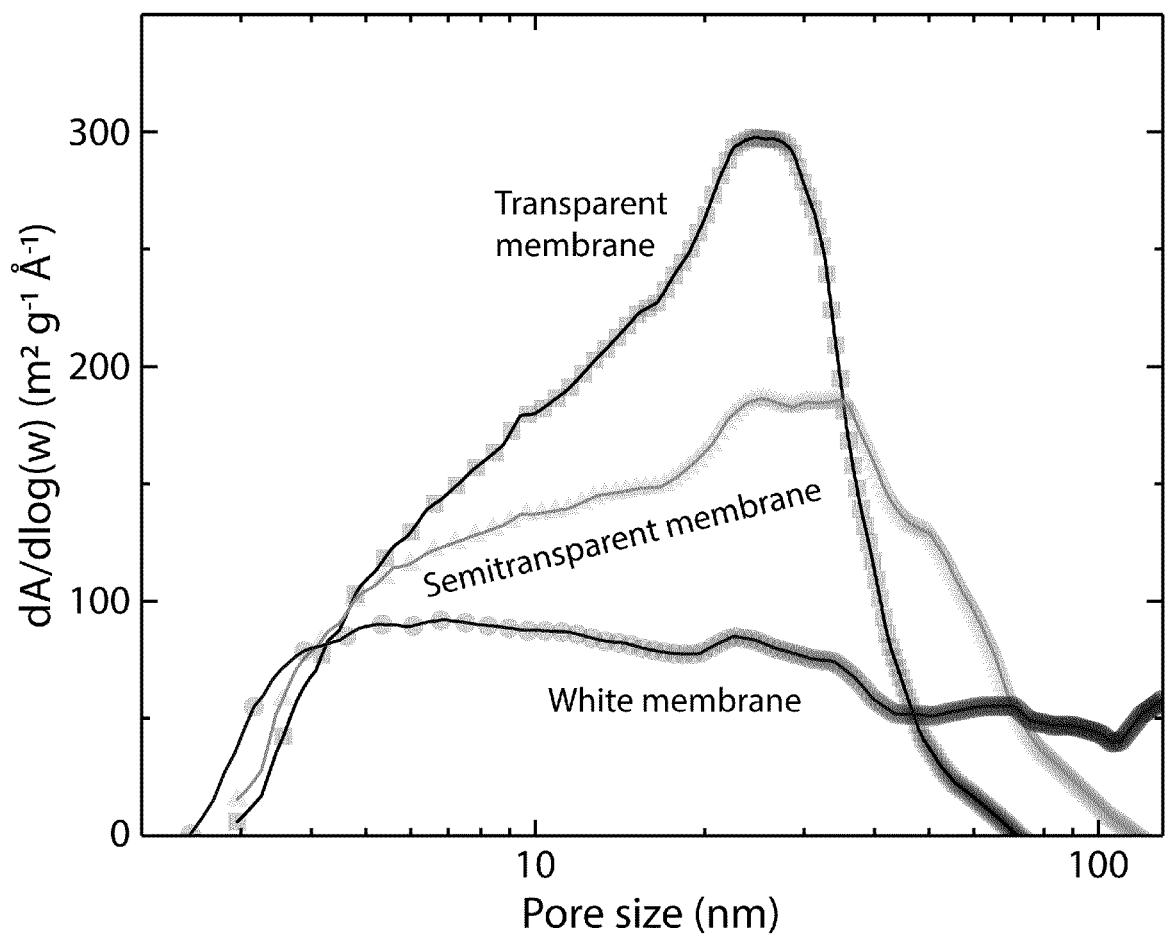
FIG. 7 is a graph illustrating the pore size distribution of the porous membranes, which have been divided into transparent membranes (squares) semi-transparent membranes (triangles), and opaque membranes (circles).
Figure 8:
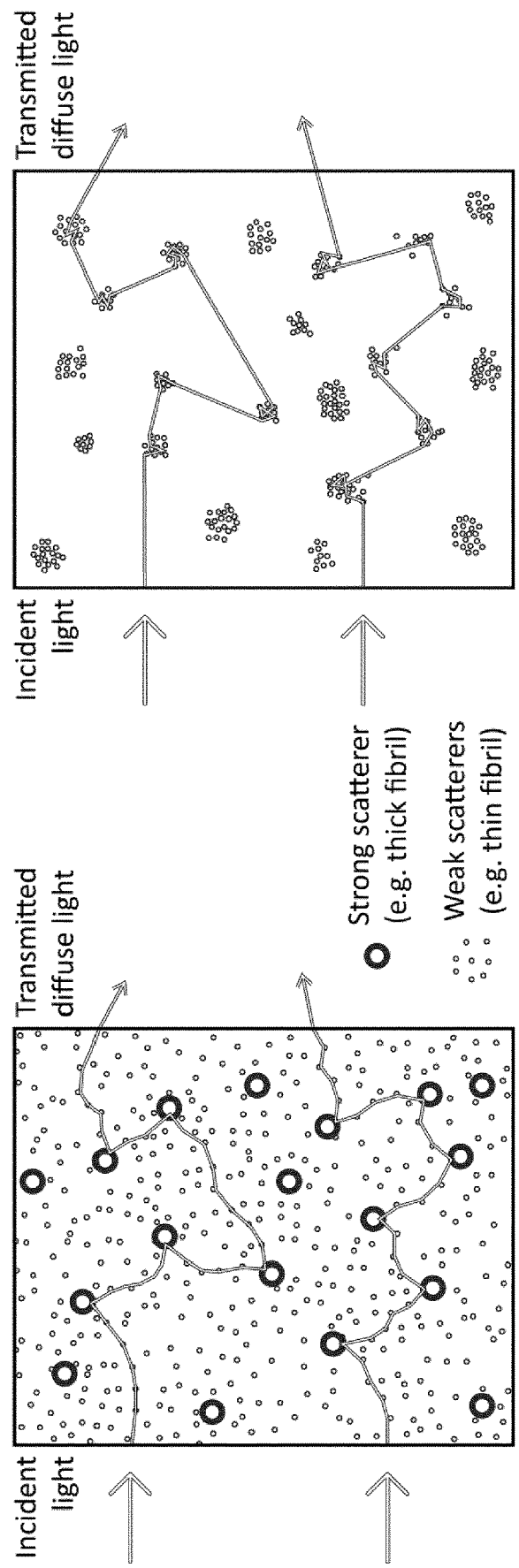
FIG. 8 is a schematic illustration of how some type of material structures may cause superdiffusion of light. On the left is a structure with randomly distributed scatterers of different scattering strengths, so that strong scatterers are fewer and therefore spaced further apart, and weak scatterers are more numerous and therefore spaced more densely. On the right is a clustered structure where collections of scatterers have formed clusters which are randomly distributed throughout the medium.

The results are shown in FIG. 7.

INDUSTRIAL APPLICABILITY

The present material can be used as a white enhancer, and generally for replacement of conventional whitening materials. Through this enhancement, the material can also be used to enhance other colours, for example in order to reduce the amount of pigment needed for strong coloration.

Possibilities for utilizing the present invention are e.g. in security printing, paints, pigments and various different kinds of coatings. Further, the present material is useful as an additive in the food and cosmetic industries, since it is based on a non-toxic material that is efficient already in small amounts.

CLAUSES

The following clauses provide embodiments of the invention:

1. A method for preparing a porous material based on fibrillar, elongated or disc-like particles, characterized by
   providing one or more fractions of colloidal particles having a diameter of 10-1000 nm,
   dispersing the colloidal particles in a solvent, and optionally concentrating the particles,
   optionally, re-dispersing the particles or changing the solvent they are dispersed in, and
   carrying out a drying step.

2. The method of clause 1, wherein the separation of fractions is achieved using centrifugation, such as a sequential centrifugation.

3. The method of clause 1 or 2, wherein the colloidal particles are selected from fibrillar, elongated, or disk-like particles, such as cellulose, chitin, algae, bamboo, synthetic or natural clay, inorganic titanium or aluminium compounds, or crystallized waxes, fats or sugars, which optionally have been bleached, the particles preferably being in the form of fibrils.

4. The method of any preceding clause, wherein the dispersion is a cellulose dispersion obtained from a cellulose pulping process, most suitably formed from birch pulp.

5. The method of any preceding clause, wherein the one or more fractions of colloidal particles are dispersed in a volatile solvent, preferably in octane, most suitably to a concentration of 5 wt. % or less.

6. The method of any preceding clause, wherein the dispersion is concentrated to a particle content of 5 wt. % or more, preferably 10 wt. % or more, and most suitably 20 to 50 wt. %.

7. The method of any preceding clause, wherein one or more fractions of colloidal particles having a diameter of 10 to 1000 nm, preferably an average diameter or thickness of about 250 nm, according to the lognormal distribution, are separated from the dispersion.

8. The method of any preceding clause, wherein the material is recovered as a powder or applied into a layer to form a film.

9. The method of any preceding clause, wherein the material is applied into a layer to form a film, typically before the final drying step, to obtain a concentrated wet gel cake.

10. The method of any preceding clause, wherein colorants or aromatics are added, preferably to the desired fractions of colloidal particles.

11. A porous fibril-based material formed of fibrillar, elongated or disc-like colloidal particles, at least a fraction having a diameter of 10-1000 nm, and air or another ambient gas, having a porosity of 20% or more.

12. The material of clause 11, wherein the particles are formed of cellulose, chitin, algae, bamboo, synthetic or natural clay, inorganic titanium or aluminium compounds, or crystallized waxes, fats or sugars, preferably having a diameter or thickness of 10 to 1000 nm, preferably 150 to 500 nm, most suitably an average diameter or thickness of about 250 nm, according to the lognormal distribution.

13. The material of clause 11 or 12, which contains 20-80% by volume of solids, preferably with a maximum of 70% by volume of solids, most suitably approximately 50%.

14. The material of any of clauses 11 to 13, having a density in the range between 10 and 1400 kg m$^{-3}$, preferably between 400 and 950 kg m$^{-3}$.

15. The material of any of clauses 11 to 14, which is in the form of membrane having a thickness of 0.1 to 100 µm, preferably 3 to 50 µm.

16. The material of any of clauses 11 to 14, which is in the form of a powder.

17. The material of any of clauses 11 to 16, having a total transmittance of less than 90% for a material thickness of 10 µm, typically a total transmittance of less than 70%, preferably a total transmittance of less than 50%, more preferably a total transmittance of less than 30%, and most suitably a total light transmittance of less than 10%, as measured using a wavelength of 500 nm.

18. The material of any of clauses 11 to 17, having a total reflectance of more than 40% for a material thickness of 2.5 µm, or a total reflectance of more than 30% for a material thickness of 10 µm, typically a total reflectance of more than 50% for a material thickness of 10 µm, preferably a total reflectance of more than 70% for a material thickness of 10 µm, and most suitably a total reflectance of more than 90% for a material thickness of 10 µm.

19. The material of any of clauses 11 to 19, manufactured using the method according to any of claims 1 to 10.

20. Use of the material of any of clauses 11 to 19, or prepared according to the method of any of claims 1 to 10, as pigment, colour, white enhancer or paint, or as protective films, or in cosmetics or medicaments, or as a light-harvesting component in solar cells.

CITATION LIST

All documents mentioned in this specification are incorporated herein by reference in their entirety.

Patent Literature
   US2015234098

Non-Patent Literature
   Bettini S, Boutet-Robinet E, Cartier C, et al (2017) Food-grade TiO2 impairs intestinal and systemic immune homeostasis, initiates preneoplastic lesions and promotes aberrant crypt development in the rat colon.
   Caixeiro S, Peruzzo M, Onelli O D, et al (2017) Disordered Cellulose-Based Nanostructures for Enhanced Light Scattering. ACS Appl Mater Interfaces 9:7885-7890.
   Fang Z, Zhu H, Yuan Y, et al (2014) Novel nanostructured paper with ultrahigh transparency and ultrahigh haze for solar cells. Nano Lett 14:765-773.
   Toivonen et al. (2015) Ambient-Dried Cellulose Nanofibril Aerogel Membranes with High Tensile Strength and Their Use for Aerosol Collection and Templates for Transparent, Flexible Devices. Adv. Funct. Mater. 25: 6618-6626

The invention claimed is:
1. A method for preparing a porous fibril-based material, characterized by
   providing fibrillar or elongated colloidal cellulose particles in solution;
   separating the colloidal cellulose particles into fractions including a fraction having colloidal cellulose particles having diameters in the range of 150 to 500 nm;
   dispersing the fraction of colloidal cellulose particles having diameters from 150 to 500 nm in water to give an aqueous mixture;

filtering the resulting aqueous mixture, and optionally concentrating the colloidal cellulose particles, dispersing the colloidal cellulose particles in a volatile solvent; and carrying out a drying step, wherein the porous fibril-based material comprises:

fibrillar or elongated colloidal cellulose particles, wherein the fibrillar or elongated colloidal cellulose particles consist of fibrillar or elongated colloidal cellulose particles having diameters from 150 nm to 500 nm, wherein the fibrillar or elongated colloidal cellulose particles form a distribution of particles having diameters from 150 nm to 500 nm with an average diameter of about 250 nm, according to the lognormal distribution, and air or another ambient gas in the pores of the material between the particles, the material having a porosity of 20% or more, a density of between 400 and 950 kg/m$^3$ and 20% to 80% by volume of solids, the material having a total reflectance of more than 70% for a material thickness of 10 μm, and the material having a total transmittance of less than 50% for a material of 10 μm, as measured using a wavelength of 500 nm, wherein the material is in the form of a membrane having a thickness of 0.1 to 100 μm.

2. The method of claim 1, wherein the aqueous mixture is filtered followed directly by dispersing the colloidal cellulose particles in a volatile solvent.

3. The method of claim 1, wherein the separation of fractions is achieved using centrifugation.

4. The method of claim 1, wherein the fraction of colloidal cellulose particles dispersed in a volatile solvent to a concentration of 5 wt. % or less.

5. The method of claim 1, wherein the colloidal cellulose particles are obtained from a cellulose pulping process.

6. The method of claim 1, wherein the aqueous mixture is concentrated to a particle content of 5 wt. % or more.

7. The method of claim 1, wherein colorants or aromatics are added to the fractions of colloidal cellulose particles.

8. A porous fibril-based material comprising:

fibrillar or elongated colloidal cellulose particles, wherein the fibrillar or elongated colloidal cellulose particles consist of fibrillar or elongated colloidal cellulose particles having diameters from 150 nm to 500 nm, wherein the fibrillar or elongated colloidal cellulose particles form a distribution of particles having diameters from 150 nm to 500 nm with an average diameter of about 250 nm, according to the lognormal distribution; and air or another ambient gas in the pores of the material between the particles, the material having a porosity of 20% or more, a density of between 400 and 950 kg/m$^3$ and 20% to 80% by volume of solids, the material having a total reflectance of more than 70% for a material thickness of 10 μm, and the material having a total transmittance of less than 50% for a material of 10 μm, as measured using a wavelength of 500 nm, wherein the material is in the form of a membrane having a thickness of 0.1 to 100 μm.

9. The material of claim 8, having a total reflectance of more than 40% for a material thickness of 2.5 μm.

10. A pigment, a colour enhancer or paint, a white enhancer or paint, a protective film, a cosmetic, a medicament, or a light-harvesting component in solar cells, comprising the material of claim 8.

11. The material of claim 8, which contains a maximum of 70% by volume of solids.

12. The material of claim 8 which contains approximately 50% by volume of solids.

13. The material of claim 8, wherein the membrane has a thickness of 3 to 50 μm.

14. The material of claim 8, having a total transmittance of less than 30% for a material thickness of 10 μm, as measured using a wavelength of 500 nm.

15. The material of claim 8, having a total transmittance of less than 10% for a material thickness of 10 μm, as measured using a wavelength of 500 nm.

16. The material of claim 8, having a total reflectance of more than 90% for a material thickness of 10 μm.

17. The material of claim 8, wherein the material has a specific surface area within the range of 100 to 140 m$^2$/g.

* * * * *